United States Patent
Hui et al.

(10) Patent No.: US 7,600,284 B2
(45) Date of Patent: Oct. 13, 2009

(54) POWERED TOOTHBRUSH HAVING A DECORATIVE FACADE

(75) Inventors: Fung Kut Hui, Hong Kong (HK); Joseph Edward Fattori, Mendham, NJ (US); Tau Dai, Edison, NJ (US); John J. Gatzemeyer, Hillsborough, NJ (US)

(73) Assignee: Colgate-Palmolive, New York, NY (US)

( * ) Notice: Subject to any disclaimer, the term of this patent is extended or adjusted under 35 U.S.C. 154(b) by 0 days.

(21) Appl. No.: 10/995,015

(22) Filed: Nov. 22, 2004

(65) Prior Publication Data

US 2005/0125920 A1    Jun. 16, 2005

Related U.S. Application Data

(63) Continuation of application No. 10/145,195, filed on May 14, 2002, now abandoned.

(51) Int. Cl.
    *A61C 17/22*    (2006.01)
(52) U.S. Cl. ............................. 15/22.1; 15/105; D4/107
(58) Field of Classification Search ................ 15/167.1, 15/257.01, 143.1, 246, 22.1, 105; 206/362.3, 206/457; 248/309.1; D4/104–112, 113, D4/101; 211/65; 29/527.2, 428, 527.1
    See application file for complete search history.

(56) References Cited

U.S. PATENT DOCUMENTS

| | | | |
|---|---|---|---|
| D113,744 S | 3/1939 | Kahn | |
| 2,446,955 A | 8/1948 | Robey | |
| D155,668 S | 10/1949 | Zanberg et al. | |
| D175,198 S | 7/1955 | Tasner et al. | |
| D209,574 S | 12/1967 | Zandberg et al. | |
| D237,659 S | 11/1975 | Meyer et al. | |
| 5,115,530 A | 5/1992 | Distiso | |
| D329,948 S | 10/1992 | Hanner | |
| D347,146 S | 5/1994 | Harrison | |
| D347,147 S | 5/1994 | Harrison | |
| D347,148 S | 5/1994 | Harrison | |
| 5,341,534 A | 8/1994 | Serbinski et al. | |
| 5,353,464 A | 10/1994 | Atkins et al. | |
| D361,433 S | 8/1995 | Yang | |
| D363,166 S | 10/1995 | Perrine | |
| 5,504,959 A * | 4/1996 | Yukawa et al. ............... | 15/22.1 |
| 5,573,019 A | 11/1996 | Hempel | |
| 5,590,436 A * | 1/1997 | Wright et al. ................. | 15/105 |
| D402,119 S | 12/1998 | Landauer | |
| 6,000,083 A * | 12/1999 | Blaustein et al. ............... | 15/28 |
| 6,026,532 A | 2/2000 | Catanzaro | |
| D423,224 S | 4/2000 | Sale et al. | |
| 6,102,203 A | 8/2000 | Marro | |
| 6,148,462 A | 11/2000 | Zseng | |
| D434,907 S | 12/2000 | Landauer | |
| 6,202,242 B1 * | 3/2001 | Salmon et al. ............... | 15/22.1 |
| D440,766 S | 4/2001 | Hartwein et al. | |
| D443,765 S | 6/2001 | Porter | |
| 6,305,083 B1 * | 10/2001 | Rijken et al. ................. | 30/43.6 |
| D452,380 S * | 12/2001 | Cheong et al. ............... | D4/107 |
| D452,381 S | 12/2001 | Cheong et al. | |
| D452,382 S | 12/2001 | Cheong et al. | |
| D452,775 S | 1/2002 | Wright | |

(Continued)

Primary Examiner—Shay L Karls
(74) Attorney, Agent, or Firm—Amy M. Fernandez

(57) ABSTRACT

The present invention relates to a powered toothbrush containing a decorative facade, which facade may be permanently attached to the brush handle or may be replaceable by the user.

29 Claims, 2 Drawing Sheets

U.S. PATENT DOCUMENTS

| | | |
|---|---|---|
| D453,996 S | 3/2002 | Kling et al. |
| D455,010 S | 4/2002 | Kling |
| 6,363,568 B1 | 4/2002 | Harrison et al. |
| D461,642 S * | 8/2002 | Blaustein et al. .............. D4/107 |
| 6,506,465 B1 | 1/2003 | Sloot |
| D475,534 S * | 6/2003 | Cunniffe et al. .............. D4/107 |
| 6,594,863 B2 * | 7/2003 | Spooner ....................... 16/436 |
| 6,742,215 B2 * | 6/2004 | Panfili et al. ............. 15/236.01 |
| D494,764 S | 8/2004 | Berde |
| 6,779,216 B2 * | 8/2004 | Davies et al. ................ 15/22.1 |
| 2003/0166373 A1 * | 9/2003 | Whitney et al. ............... 446/71 |

* cited by examiner

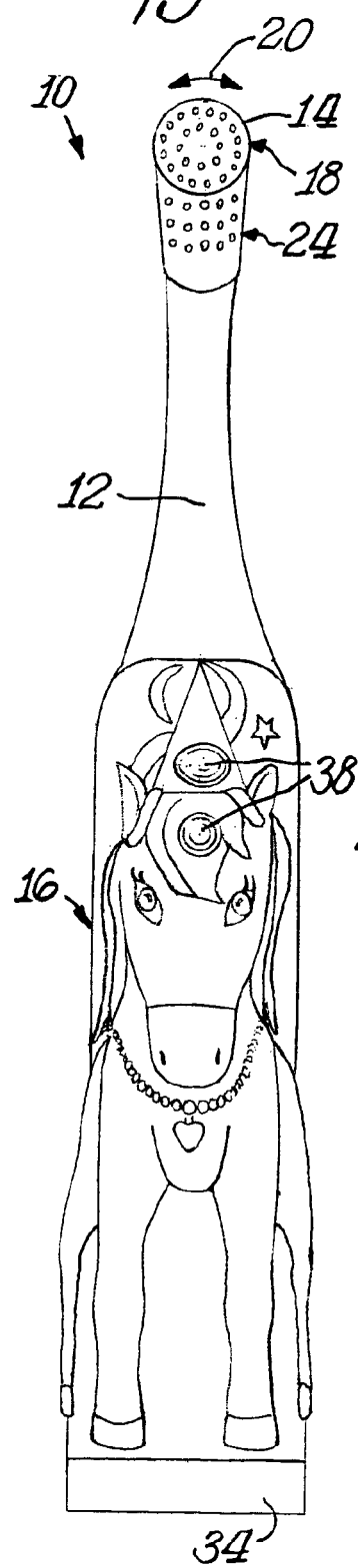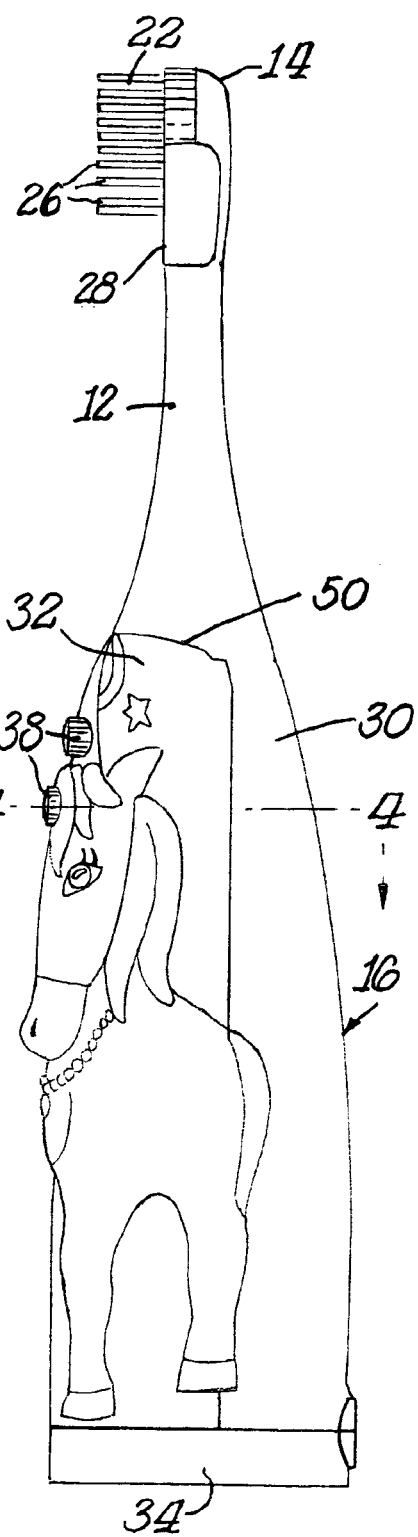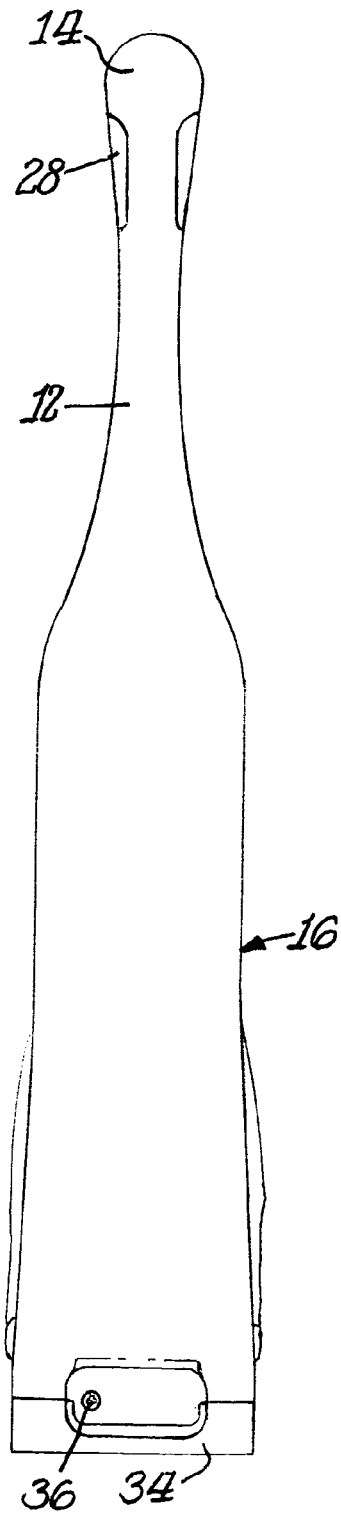

POWERED TOOTHBRUSH HAVING A DECORATIVE FACADE

CROSS-REFERENCE TO RELATED APPLICATIONS

This is a continuation of U.S. application Ser. No. 10/145,196, filed May 14, 2002 now abandoned.

BACKGROUND OF THE INVENTION

A. Field of the Invention

The present invention relates generally to toothbrushes, and, more particularly, to an economical powered toothbrush assembly having a standardized handle with a recess for receiving and retaining alternative decorative facades in such a manner that there is a smooth interface therebetween.

B. Description of the Related Art

Various types of non-powered toothbrushes having object-shaped handles are generally known in the art, and are designed to provide ergonomic grips, aesthetically pleasing appearances and/or to appeal to children to encourage them to brush their teeth for enhanced oral health. Examples of such toothbrushes that appeal to children include U.S. Design Pat. Nos. 443,765 and 452,381, which disclose toothbrushes which incorporate vehicles and U.S. Design Pat. Nos. 434,907, 5,353,464 which incorporate animals. Other toothbrush designs containing human, or toy shapes which appeal to children are disclosed in U.S. Design Pat. Nos. 113,744, 155,668, 175,198, and 209,574.

Many powered toothbrushes include handles formed by connecting two body portions or shells to form a complete housing. Examples of such powered toothbrushes may be found in U.S. Pat. Nos. 5,115,530, 5,341,534, and 6,148,462, 6,202,242. U.S. Pat. No. 6,202,242 discloses a light-emitting, electric toothbrush that includes a handle made from a front body portion and a rear body portion. The front and rear body portions are ultrasonically bonded together along an interface line, to permanently seal the two body portions. None of the aforementioned toothbrushes discloses joining a third shell section, i.e. a decorative facade, about the exterior of a standardized powered toothbrush handle.

U.S. Pat. No. 5,590,436 discloses a non-powered toothbrush having a handle that carries a figurine formed separately from but attached to the handle. The figurine can be attached directly to the handle of the toothbrush or can be attached first to a carrier, which carrier is then attached to the handle. The toothbrush handle of U.S. Pat. No. 5,590,436 does not disclose use of a decorative facade about the exterior of an otherwise complete toothbrush handle.

Thus, there is a need in the art to provide powered toothbrushes which having a facade for economic, ergonomic and/or aesthetic reasons, especially facades designed to appeal to children to encourage them to brush their teeth.

SUMMARY OF THE INVENTION

The present invention solves the problems of the related art by providing a powered toothbrush having a standardized handle to provide manufacturing efficiency and economy, to which standardized handle alternate facades may be permanently or removably and replaceably mounted. The decorative facade may have designs that appeal to children, to motivate them to brush their teeth often, and to set in place lifelong habits of good oral hygiene.

Alternatively, the decorative facade may be used as a location for advertising material. The powered toothbrush may then be sold to a variety of manufactures, who in turn, may place their own unique identification or advertising material on the decorative facade. Such manufacturers may then offer the powered toothbrushes, with their unique facade, as promotional items for their companies and/or their products.

As embodied and broadly described herein, the present invention is broadly drawn a powered toothbrush assembly, comprising: a head connected to a neck, said head having a plurality of bristles extending outwardly therefrom; and a handle connected to said neck, said handle having a decorative facade mounted thereon. The decorative facade may be permanently or replaceably mounted within a recessed portion of the handle so as to smoothly conform to the external shape of said handle, to enhance the consumer acceptance thereof.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a front elevational view of a powered toothbrush having a recess for retaining a decorative facade in accordance with an embodiment of the present invention;

FIG. 2 is a right side elevational view of the powered toothbrush shown in FIG. 1;

FIG. 3 is a rear elevational view of the powered toothbrush shown in FIGS. 1 and 2;

DETAILED DESCRIPTION OF EMBODIMENTS OF THE INVENTION

Figure 4:
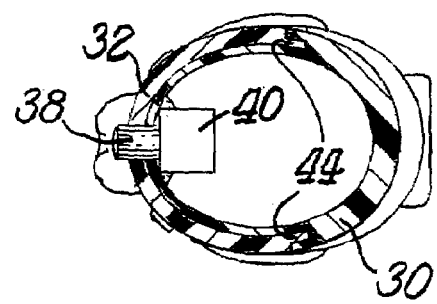
FIG. 4 is a cross-sectional top plan view of the powered toothbrush handle shown in FIGS. 1-3, taken along line 4-4 of FIG. 2.

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

FIGS. 1-6 illustrate one practice of the present invention wherein a powered toothbrush 10 includes a neck section 12 interposed between a head 14 and a handheld handle 16. Preferably, neck 12 and head 14 are integrally connected, and together are detachably connected to handle 16 so that head 14 may be replaced as the bristles become worn. In an alternate, less costly embodiment of the present invention, the head 14 and neck 12 are integral and permanently connected to the handle 16. Head 14 may contain a movable bristle bearing platform or a tuft block in a variety of shapes, including but not limited to circular, oval, square, rectangular, various regular or irregular shapes, etc.

As illustrated, particularly in FIG. 1, head 14 includes a first movable tuft block 18, which is illustrated as being at the outermost or distal portion of head 14. First tuft block 18 is preferably a disk of circular ring-type shape, and is movably driven in a rotating or oscillating manner as indicated by arrow 20 in FIG. 1. Other shapes may be used for first tuft block 18, such as oval or various regular of irregular shapes. First tuft block 18 may be provided with a multitude of tufts or bristles 22, arranged, in the illustrated embodiment, in a circular manner. Bristles 22 extend generally away from an outer surface 28 of head 14.

First tuft block 18 may be oscillated by any suitable drive mechanism. For example, the drive mechanism described in U.S. Pat. No. 5,625,916, the disclosure of which being incorporated by reference herein in its entirety except where inconsistent with the express teachings of the present invention, may be used to oscillate first tuft block 18.

A second tuft block 24 may be fixedly attached to head 14 at a location above neck 12, but below first tuft block 18. Second tuft block 24 may include a multitude of tufts or bristles 26 extending away from outer surface 28 of head 14 a distance equal to or different than the distance bristles 22 extend outwardly from outer surface 28 of head 14. It is to be understood, however, that second tuft block 24 could be located distally from, or laterally side-by-side to first tuft block 18. It is preferred, however, that second tuft block 24 be longitudinally outside of first tuft block 18 so as to extend the length of the surface area of head 14 having bristles.

The provision of second tuft block 24 in this manner is advantageous in that powered toothbrush 10 simulates, in appearance of head 14, the structure of a manual toothbrush. This makes powered toothbrush 10 more acceptable to users of conventional manual toothbrushes, since the appearance simulates what such a user is accustomed to seeing. In addition, two tuft blocks 18, 24 even further enhances the efficiency of toothbrush 10, both as a result of the movement of tuft blocks 18, 24, and of the ability to readily retain toothpaste.

While FIGS. 1 and 2 illustrate conventional fiber or filament form bristles, the term "bristles" as used herein is intended to be used in a generic sense as cleaning elements or massage elements and could include, for example, elastomeric fingers or walls arranged in a circular cross-section shape or any type of desired shape, including straight portions or sinusoidal portions.

The bristles 22, 26 could be mounted to the tuft blocks or sections by extending through suitable openings in outer surface 28 so that the base of bristles 22, 26 is mounted within or below the surface 28 using conventional staple or in-mold tufting technology for mounting therein. If desired, the bristles could be embedded in an elastomeric material which would permit the bristles to have an independent motion. Such various forms of bristles may thus be used for the bristles used in any section of head 14.

It is to be understood that the specific illustration of the bristles is merely for exemplary purposes. The invention can, however, be practiced with various combinations of the same or different bristle configurations as disclosed in U.S. Pat. Nos. 5,609,890, 5,390,984, and 5,533,791, the disclosures of which being incorporated by reference herein in their entirety, and/or with the same or different bristle materials, such as nylon bristles, spiral bristles, rubber bristles, etc. Similarly, while FIGS. 1 and 2 illustrate the bristles to be generally perpendicular to surface 28 of head 14, some or all of the bristles may be angled at various angles with respect to the outer surface of the bristle head. It is thereby possible to select the combination of bristle configurations, bristle materials and bristle orientations to achieve specific intended results, such as to create as much movement from the oscillating tuft heads to deliver additional oral health benefits like enhanced cleaning, tooth polishing, tooth whitening and/or massaging of the gums.

As further shown in FIGS. 1-6, handle 16 preferably includes a housing 30 and a decorative facade 32, each molded of known plastics, including for example a copolymer such as ABS (acrylonitrile, butadiene, styrene copolymer) or a high impact styrene. The decorative facade 32 can be removably or permanently connected to housing 30, by means discussed below. Housing 30 can be pre-formed as a single generally hollow shell or as two or more separate shell portions which are joined together by welding or other known means. Pre-forming housings or pre-forming complete powered toothbrushes to accept alternative decorated facades provides for an efficient less costly manufacturing process, in that the preformed housings or complete powered toothbrushes can be manufactured in longer manufacturing runs which have less wastage and less set-up labor cost than short manufacturing runs in which a decorative front is altered.

Housing 30 has an opening provided at an end portion thereof located away from neck 12. The hollow nature of housing 30, as best be seen in FIG. 4, enables housing 30 to enclose the drive mechanism (not shown) for oscillating first tuft block 18, as well as, the mechanism(s) providing power to the drive mechanism. The opening of housing 30 may be enclosed by an end cap or base 34. Base 34 enables a power mechanism, batteries for example, to be inserted in or removed and replaced from housing 30. Base 34 connects to housing 30 via a variety of connection mechanisms which may include a force fit male/female type interlock or as illustrated in FIG. 3, a hinged screwed 36 door which allows access to pry-off the end cap 34.

Handle 16 is also provided with buttons 38 for controlling the drive mechanism of the powered toothbrush 10. As best shown in FIGS. 1 and 2, buttons 38 extend through openings 33 (see FIG. 5) provided in decorative facade 32. Buttons 38 may control the drive mechanism, and thus the oscillation of first tuft block 18, in a known on-off type manner. Although two buttons 38 are shown in the Figures, preferably one to energize the drive mechanism and one to de-energize the drive mechanism, buttons 38 may be replaced with single switch or other control mechanism for the drive mechanism. As best shown in FIG. 4, each button 38 may connect to a switch 40 that controls the energizing of the drive mechanism.

Figure 5:
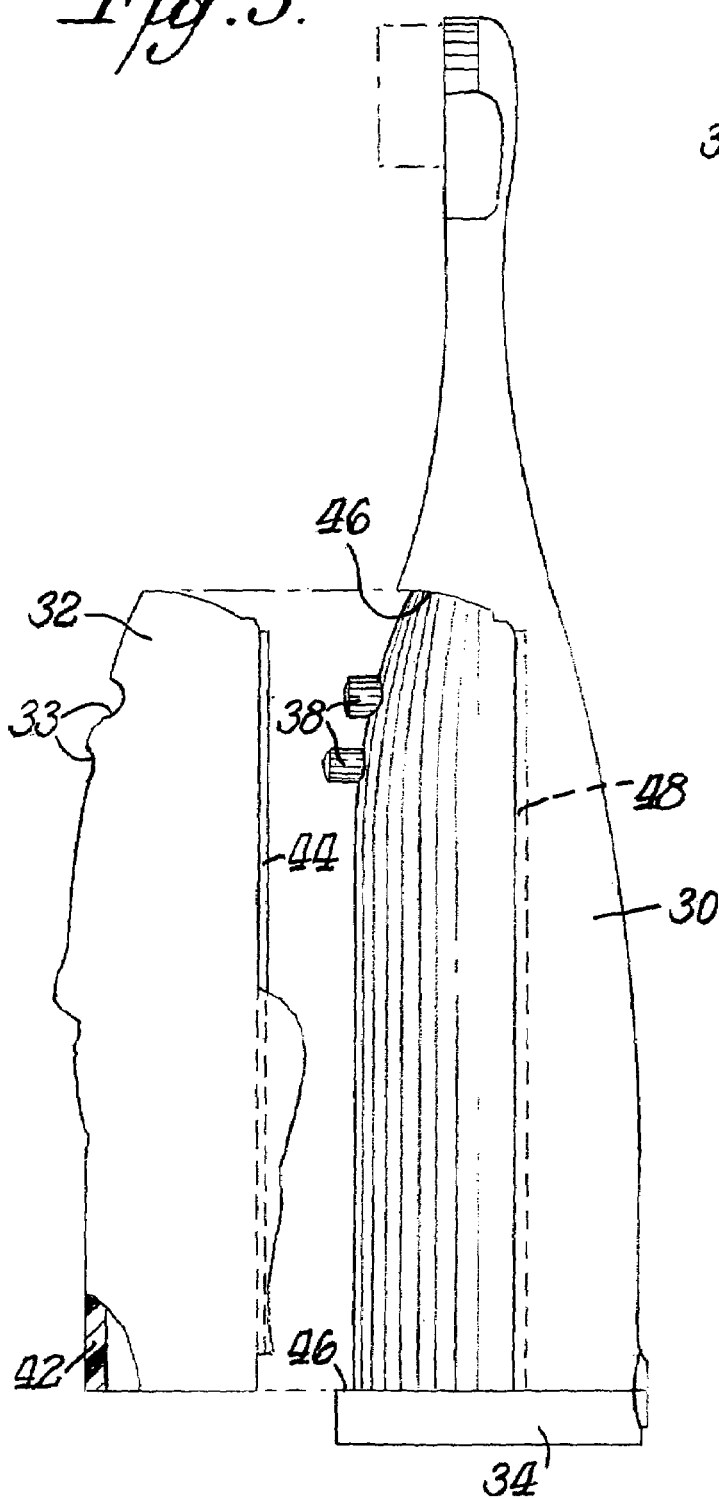
FIG. 5 is a right side elevational view of the powered toothbrush shown in FIGS. 1-4, with the decorative facade spaced apart from the remainder thereof.
Figure 6:
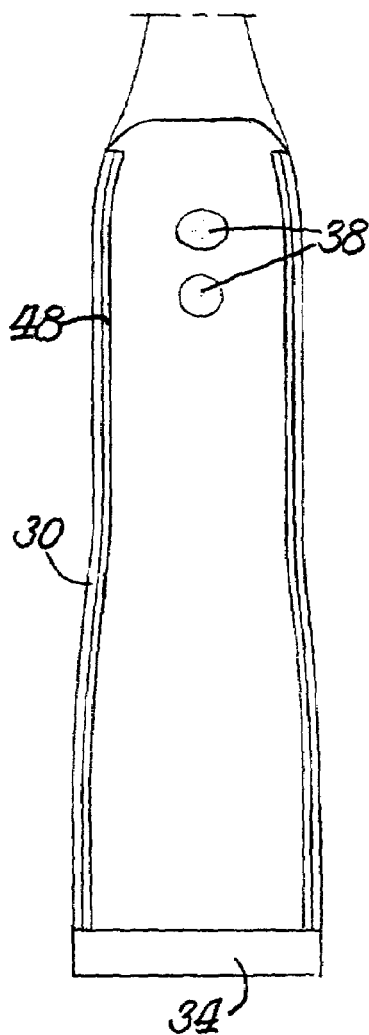
FIG. 6 is a fragmental front elevational view of the powered toothbrush handle shown in FIGS. 1-5, with the decorative facade removed.

Further details of the housing 30 and decorative facade 32 are provided in FIGS. 4-6. As best shown in FIG. 5, decorative facade 32 includes a body portion 42 that is arcuate in shape and conforms to the arcuate shape of housing 30. Body portion 42 includes thinner sections 44 at the distal ends thereof. Preferably the thinner sections 44, as shown, extend substantially along the entire height of body portion 42; however, these sections may only extend a portion of the length thereof. The thinner sections 44 are received in the recessed portion of housing 30, as described more fully below.

Housing 30 preferably includes a recessed portion 46 that is arcuate in shape and conforms to the arcuate shape of decorative facade 32. As shown in FIGS. 4 and 5, buttons 38 extend through openings provided in recessed portion 46 of housing 30, and through openings 33 provided in decorative facade 32. Recessed portion 46 of housing 30 may further include deeper sections or grooves 48 that receive and retain thinner sections 44 of decorative facade 32. Thus, deeper sections 48 may extend substantially along the entire height of recessed portion 46 corresponding to the thinner sections 44 extending from decorative facade 32 to interconnect therewith. The interconnection of thinner sections 44 of decorative facade 32 and deeper sections 48 of housing 30 is best shown in FIG. 4. This interconnection enables decorative facade 32 to be mechanically, by a force or snap fit, and removably attached to housing 30.

Alternatively, decorative facade 32 may be permanently attached to housing 30 in a variety of ways. For example, decorative facade 32 may be ultrasonically or adhesively, using cold or hot adhesives, bonded to recessed portion 46 of housing 30 along an interface line 50, as shown in FIG. 2. Decorative facade 32 may also be connected to recessed portion 46 with a mechanical connector (nuts and bolts, screws, etc.), heat or laser welded, etc.

The decorative facade 32 may have a three dimensional design, such as the horse illustrated in FIGS. 1-2, or alternately a vehicle, or a soldier, or a fireman, or a policeman or other image that appeals to children and that can be used by a child in play as a toy. A powered toothbrush 10 having a handle recess 46 with such a toy-shaped, decorative facade 32 provided therein offers a fun and exciting way for children to brush their teeth. Such excitement motivates children to brush their teeth often, to set in place lifelong habits of good oral hygiene.

Alternatively, the decorative facade 32 may be used as a location for advertising material. The powered toothbrush 10 may then be sold to a variety of manufactures, who in turn, may place their own unique advertising material on the decorative facade 32. Such manufacturers may then offer the powered toothbrushes 10, with their unique facade 32, as promotional items for their companies and/or their products.

What is claimed is:

1. A toothbrush assembly, comprising:
   a head having a plurality of tooth cleaning elements extending outwardly there from;
   a handle connected to said head and defining a longitudinal axis, said handle having a housing having an external shape, and the housing substantially enclosing an internal chamber; wherein the housing includes a recessed portion having a substantially convex outer surface, the recess portion being opposite the internal chamber;
   a decorative facade removably secured to the housing within the recessed portion, the decorative facade having an outer surface;
   wherein the decorative facade includes a substantially concave inner surface having a curvature corresponding to the outer surface of the recessed portion of the handle, and wherein the decorative facade includes a thickness corresponding to a depth of the recessed portion of the housing in a longitudinal and transverse direction;
   wherein a first one of the housing and the decorative facade includes at least one non-circular longitudinally-extending groove formed therein for receiving at least one mating non-circular longitudinally-extending flange member in a corresponding second one of the housing and the facade;
   wherein the at least one groove is received in the flange member, such that a portion of the outer surface of the facade is substantially flush with the outer surface of the handle; and
   wherein a portion of the facade extends outwardly in the same direction as the tooth cleaning elements such that said handle and facade together are adapted to accommodate a grip of a user.

2. The toothbrush assembly of claim 1, wherein said handle is arcuate in shape.

3. The toothbrush assembly of claim 1, wherein the at least one groove receives and retains the at least one flange member of said decorative facade, enabling said decorative facade to be removably attached to said handle.

4. The toothbrush assembly of claim 3, wherein said decorative facade contains a raised feature extending beyond an outer surface of the housing.

5. The toothbrush assembly of claim 3, wherein said decorative facade is removably connected to said handle via a force fit.

6. The toothbrush assembly of claim 3, wherein said decorative facade is removably connected to said handle via a snap fit.

7. The toothbrush assembly of claim 1, wherein a three-dimensional design of the facade enhances the grippability of the handle.

8. The toothbrush assembly of claim 1, wherein the design of the facade is three-dimensional having at least two changes in elevations with respect to the housing.

9. The toothbrush of claim 1, wherein the non-circular longitudinally-extending groove extends along substantially an entire longitudinal side of one of either the housing or facade.

10. The toothbrush of claim 9, further comprising a second non-circular longitudinally-extending groove that extends along substantially an entire second longitudinal side of one of either the housing or facade, the two grooves being arranged in substantially parallel relationship to each other and extending along the longitudinal axis of the handle.

11. The toothbrush of claim 1, wherein the at least one longitudinally-extending groove has a length measured in the direction of the longitudinal axis of the handle that is greater than a depth of the groove measured transverse to the longitudinal axis.

12. The toothbrush of claim 1, wherein the decorative facade is removably secured to the handle solely via a snap fit between the groove and the flange.

13. A toothbrush assembly, comprising:
   a head having a plurality of tooth cleaning elements extending outwardly there from;
   an actuator for controlling powered movement of a portion of at least a portion of the tooth cleaning elements;
   an elongated handle connected to the head and defining a longitudinal axis, the handle having a housing with an external shape, the housing substantially enclosing an internal chamber and further including a recessed portion having a substantially convex outer surface and two opposing longitudinally-extending sides, the recess portion being opposite the internal chamber, and the actuator projecting through the housing within the recessed portion;
   a decorative facade removably secured to the housing and having two opposing longitudinally-extending sides configured to correspond to the sides of the recessed portion of the handle, the decorative facade having a contoured outer surface and a substantially concave inner surface corresponding to a convexity of the outer surface of the recessed portion of the housing, and the decorative facade further having a thickness corresponding to a depth of the recessed portion of the handle in a longitudinal direction and in a transverse direction, such that the decorative facade and the edges of the recess of the housing form a flush connection;

wherein the actuator extends outwardly from the outer surface of the recessed portion of the handle a sufficient distance to project through an opening in the decorative facade and extend away from the outer surface of the decorative facade;

wherein a first one of the housing and the decorative facade includes at least one longitudinally-extending groove formed along one of the longitudinally-extending sides of either the housing or facade for receiving a complementary configured longitudinally-extending flange member in a corresponding second one of the housing and the facade.

14. The toothbrush assembly of claim 13, wherein a portion of the outer surface of the facade is substantially smooth with the outer surface of the handle; and a portion of a contour of the facade extends outwardly in the direction of the tooth cleaning elements.

15. The toothbrush assembly of claim 13, wherein the design of the decorative facade contains a raised feature extending beyond an outer surface of the housing and wherein the actuator is disposed through an opening in the raised feature.

16. The toothbrush assembly of claim 13, wherein the actuator forms a part of a design on the outer surface of the decorative facade.

17. The toothbrush assembly of claim 13, wherein the groove retains the flange member of the decorative facade, enabling the decorative facade to be removably attached to the handle.

18. The toothbrush of claim 13, wherein the at least one longitudinally-extending groove has a length measured in the direction of the longitudinal axis of the handle that is greater than a depth of the groove measured transverse to the longitudinal axis.

19. The toothbrush of claim 13, wherein the longitudinally-extending groove is elongated in the direction of the longitudinal axis of the handle.

20. The toothbrush of claim 13, wherein the longitudinally-extending groove is formed in the housing.

21. The toothbrush of claim 13, wherein the longitudinally-extending groove extends along substantially an entire length of one of the longitudinally-extending sides of either the housing or facade.

22. The toothbrush of claim 13, further comprising a second longitudinally-extending groove formed therein along a respective one of the longitudinally-extending sides of either the housing or facade for receiving a second complementary configured longitudinally-extending flange member formed in one of the housing and the facade.

23. The toothbrush of claim 13, wherein the decorative facade is removably secured to the handle solely via a snap fit between the groove and the flange.

24. A toothbrush assembly, comprising:
a head having a plurality of tooth cleaning elements extending outwardly therefrom;
an actuator button for controlling a powered drive mechanism for movement of at least a portion of the tooth cleaning elements;
an elongated handle connected to the head and defining a longitudinal axis, the handle comprising a housing defining a recessed portion having a height and a substantially convex outer surface, the recessed portion including a pair of grooves being elongated in the direction of the longitudinal axis, the grooves having a length measured in the direction of the longitudinal axis and a narrower width;
a decorative facade removably secured to the housing and having a substantially concave inner surface corresponding to a convexity of the outer surface of the recessed portion of the housing, the decorative facade further including a body having a height and a thickness corresponding to a depth of the recessed portion of the handle in the longitudinal direction and in a transverse direction such that the decorative facade and the edges of the recess of the housing form a flush connection;
the body of the decorative facade including a pair of flanges being elongated in the direction of the longitudinal axis, the flanges having a length measured in the direction of the longitudinal axis and a narrower width,
wherein the pair of flanges and grooves are complementary configured and arranged so that the flanges are insertable into the grooves via a snap fit therebetween to removably secure the facade to the handle.

25. The toothbrush of claim 24, wherein the flanges are defined by integral thinner sections of body of the decorative facade disposed along the height of the body at distal side edges thereof.

26. The toothbrush of claim 25, wherein the flanges extend substantially along the entire height of body portion.

27. The toothbrush of claim 24, wherein the grooves are defined by deeper sections within the recessed portion of the handle housing that are disposed along distal sides edges of the recessed portion.

28. The toothbrush of claim 27, wherein the grooves extend substantially along the entire height of the recessed portion.

29. The toothbrush of claim 24, wherein the handle housing has a cylindrical or ovoid shape defining an outer circumference, the decorative facade circumferentially extending at least halfway around the circumference of the handle housing when attached thereto.

* * * * *